United States Patent [19]

Jautelat et al.

[11] Patent Number: 5,041,459
[45] Date of Patent: Aug. 20, 1991

[54] MICROBICIDAL HYDROXY-KETO-AZOLES

[75] Inventors: Manfred Jautelat, Burscheid; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 535,270

[22] Filed: Jun. 8, 1990

[30] Foreign Application Priority Data

Jun. 28, 1989 [DE] Fed. Rep. of Germany ....... 3921163

[51] Int. Cl.$^5$ ................ A01N 43/653; C07D 249/08
[52] U.S. Cl. .................... 514/383; 514/184; 514/384; 548/263.2; 548/263.4; 548/263.8; 548/264.2; 548/264.8; 548/265.2; 548/266.4; 548/266.6; 548/266.8; 548/267.4; 548/268.6; 548/101
[58] Field of Search ............... 548/263.2, 263.4, 263.8, 548/264.2, 264.8, 265.2, 266.6, 266.4, 266.8, 267.4, 268.6, 101; 514/383, 384, 184

[56] References Cited

U.S. PATENT DOCUMENTS 4,723,984 2/1988 Holmwood et al. .................. 71/76

FOREIGN PATENT DOCUMENTS

| 0040345 | 11/1981 | European Pat. Off. |
| 114487 | 8/1984 | European Pat. Off. ........ 548/268.6 |
| 114567 | 8/1984 | European Pat. Off. ........ 548/268.6 |
| 0117578 | 9/1984 | European Pat. Off. |
| 0304552 | 3/1989 | European Pat. Off. |

OTHER PUBLICATIONS

106:213885b, Masaru Ogata et al., "Synthesis and Oral Antifungal Activity . . . ", Chem. Abstract, vol. 106, (1987), p. 655.

104:64208x, Shionogi and Co. Ltd., "Imidazole and Triazole Fungicides . . . ", Chem. Abstracts, vol. 104 (1986), p. 278.

Primary Examiner—Mary C. Lee
Assistant Examiner—Patricia L. Morris
Attorney, Agent, or Firm—Sprung Horn Kramer & Woods

[57] ABSTRACT

Microbicidal hydroxy-keto-azoles of the formula

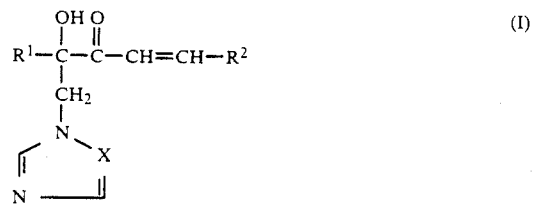

in which $R^1$ represents optionally substituted alkyl, optionally substituted alkenyl, optionally substituted cycloalkyl or optionally substituted aryl, $R^2$ represents optionally substituted aryl or a five- or six-membered heterocyclic radical having up to 3 hetero-atoms, which is optionally substituted and optionally fused to benzene, and X represents a nitrogen atom or a CH group, and addition products thereof with acids and metal salts.

10 Claims, No Drawings

MICROBICIDAL HYDROXY-KETO-AZOLES

The present invention relates to new hydroxy-keto-azoles, to a process for their preparation and to their use as microbicides in plant protection and in the protection of materials.

It is already known that numerous hydroxyethylazolyl derivatives can be used for combating fungi (cf. EP-OS (European Published Specification) 0,040,345). Thus, for example, 1-(2-chloro-phenyl)-3-(1,2,4-triazol-1yl-methyl)-4,4-dimethyl-pent-1-en-3-ol, 1-(4-fluorophenyl)-3-(1,2,4-triazol-1-yl-methyl)-4,4-dimethyl-pent-1-en-3-ol and 1-(4-methyl-phenyl)-3-(1,2,4-triazol-1-yl-methyl)-4,4-dimathyl-pent-1-en-3-ol can be employed as fungicides against phytopathogenic fungi. However, at low application rates the activity of these substances in some cases leaves something to be desired.

New hydroxy-keto-azoles of the formula

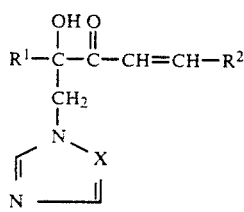  (I)

in which $R^1$ represents optionally substituted alkyl, optionally substituted alkenyl, optionally substituted cycloalkyl or optionally substituted aryl, $R^2$ represents optionally substituted aryl or a five- or six-membered heterocyclic radical having up to 3 hetero-atoms, which is optionally substituted and optionally fused to benzene, and X represents a nitrogen atom or a CH group, and their acid addition salts and metal salt complexes have now been found.

The compounds of the formula (I) contain an asymmetrically substituted carbon atom and can therefore be obtained in the two optical isomer forms.

Moreover, the substances of the formula (I) can be present in two geometrical isomer forms, depending on the position of the hydrogen atoms on the double bond. The present invention relates both to the isomer mixtures and to the individual isomers.

It has furthermore been found that hydroxy-keto-azoles of the formula (I) and their acid addition salts and metal salt complexes are obtained when, in a first step, hydroxyalkines of the formula

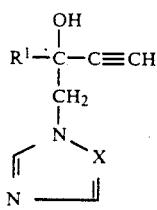  (II)

in which $R^1$ and X have the abovementioned meanings, are reacted with water in the presence of acids and/or metal catalysts and also, if appropriate, in the presence of a diluent and the resulting hydroxyketones of the formula

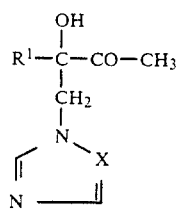  (III)

in which $R^1$ and X have the abovementioned meanings, are reacted in a second step with aldehydes of the formula $$R^3\text{—CHO} \quad (IV)$$

in which $R^2$ has the abovementioned meaning, in the presence of a diluent and if appropriate in the presence of a catalyst and if appropriate an acid or a metal salt is then adducted to the compounds of the formula (I) thus obtained.

Moreover, it has been found that the new hydroxy-keto-azoles of the formula (I) and their acid addition salts and metal salt complexes have very good microbicidal properties and can be employed both in plant protection and in the protection of materials.

Surprisingly, the substances according to the invention show a distinctly better activity in combating phytopathogenic fungi than 1-(2-chloro-phenyl)-3-(1,2,4-triazol-1-yl-methyl)-4,4-dimethyl-pent-1-en-3-ol, 1-(4-fluorophenyl)-3-(1,2,4-triazol-1-yl-methyl)-4-4-dimethyl-pent-1-en-3-ol and 1-(4-methyl-phenyl)-3-(1,2,4-triazol-1-yl-methyl)-4,4-dimethyl-pent-1-en-3-ol, which are previously known active compounds of similar constitution and with the same type of action.

Formula (I) provides a general definition of the hydroxy-keto-azoles according to the invention. Preferably, in this formula $R^1$ represents straight-chin or branched alkyl having 3 to 7 carbon atoms, where each of these radicals can be substituted by halogen, cycloalkyl having 3 to 7 carbon atoms, phenyl and/or halogenophenyl, alkenyl having 3 to 6 carbon atoms, which is optionally substituted by halogen, phenyl and/or halogenophenyl, and furthermore cycloalkyl having 3 to 7 carbon atoms, where each of these radicals can be substituted by alkyl having 1 to 4 carbon atoms, or phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, $R^2$ represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or $R^2$ represents a five-membered heterocycle having 1 to 3 nitrogen atoms and being optionally fused to benzene, a five-membered heterocycle having one sulphur atom and being optionally fused to benzene, a five-membered heterocycle having one oxygen atom and one sulphur atom and being optionally fused to benzene, a five-membered heterocycle having one oxygen atom and one nitrogen atom and being optionally fused to benzene, a five-membered heterocycle having one sulphur atom and one nitrogen atom and being optionally fused to benzene, a six-membered heterocycle having 1 to 3 nitrogen atoms and being optionally fused to benzene, where each of the abovementioned heterocyclic radicals can be monosubstituted or polysubstituted by identical or different substituents from the series comprising halogen, alkyl having 1 to 4 carbon atoms, hydroxyalkyl having 1 to 4 carbon atoms, hydroxyalkinyl having 3 to 8 carbon atoms, alkoxy having 1 or 3 carbon atoms, alkoxy having 1 or 2 carbon atoms, halogenoalkyl, halogenoalkoxy and halogenoalkylthio in each case having 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano, and X represents a nitrogen atom or a CH group.

Particularly preferred compounds of the formula (I) are those in which $R^1$ represents isopropyl, tert.-butyl, tert.-pentyl, 1-ethyl-1-methyl-propyl, 1,1-dimethyl-pentyl, 1,1,2-trimethylpropyl or 1,1-dimethyl-prop-2-enyl, where each of these abovementioned radicals can be substituted by fluorine, chlorine, bromine, phenyl, chlorophenyl, dichlorophenyl, fluorophenyl and/or difluorophenyl, furthermore 1-methyl-cyclohexyl, cyclohexyl, 1-methylcyclopropyl, cyclopropyl, 1-methylcyclopentyl, cyclopentyl or 1-ethylcyclopentyl, or phenyl which can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano, $R^2$ represents phenyl which can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano, or $R^2$ represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and/or propionyl, and X represents a nitrogen atom or a CH group.

A group of very particularly preferred compounds according to the invention are those substances of the formula (I) in which $R^1$ represents tert.-butyl, tert.-pentyl, 1-ethyl-1-methyl-propyl, 1,1,2-trimethylpropyl, 1,1-dimethyl-pentyl or 1,1-dimethyl-prop-2-enyl, where each of these radicals can be monosubstituted or disubstituted by fluorine and/or chlorine, or by phenyl, chlorophenyl and/or fluorophenyl, furthermore 1-methyl-cyclohexyl, 1-methyl-cyclopentyl or 1-ethyl-cyclopentyl, or phenyl which can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, nitro, cyano and/or methoximinomethyl, $R^2$ represents phenyl which can be monosubstituted to trisubstituted by identical or different substituents from the series comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, nitro, cyano and/or methoximinomethyl, or $R^2$ represents furanyl, thienyl, thiazolyl, pyridinyl, pyrimidinyl, quinolinyl, benzothienyl, benzothiazolyl or benzofuranyl, where each of these radicals can be monosubstituted to trisubstituted by identical or different substituents from the series comprising fluorine, chlorine, bromine, methyl, ethyl, methoxy, ethoxy, methylthio, trifluoromethyl, trifluoromethoxy, trifluoromethylthio, hydroxymethyl, 3-hydroxy-3-methylbut-1-in-1-yl, methoxycarbonyl, ethoxycarbonyl, formyl, dimethoxymethyl, methoximinomethyl, methoximino-ethyl, nitro and/or cyano, and X represents an oxygen atom or a CH group.

Preferred compounds according to the invention are also addition products of acids and those hydroxy-keto-azole of the formula (I) in which $R^1$, $R^2$ and X have the meanings which have already been mentioned as preferred for the substituents.

The acids which can be adapted preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and sulphonic acids such as, for example, p-toluenesulphonic acid and 1,5-naphthalenedisulphonic acid.

Additionally preferred compounds according to the invention are addition products of salts of metals of the main groups II to IV and subgroups I and II and also IV to VIII of the Periodic Table of the elements and those hydroxy-keto-azoles of the formula (I) in which $R^1$, $R^2$ and X have the meanings which have already been mentioned as preferred for these substituents.

In this connection, salts of copper, zinc, manganese, magnesium, tin, iron and nickel are particularly preferred. Possible anions of these salts are those which are derived from those acids which lead to physiologically tolerable addition products. Particularly preferred acids of this type in this connection are the hydrohalic acids, such as, for example, hydrochloric acid and hydrobromic acid, furthermore phosphoric acid, nitric acid and sulphuric acid.

The hydroxy-keto-azoles shown in the following table may be mentioned as specific examples of substances according to the invention.

TABLE 1

$$R^1-\underset{\underset{\underset{N}{\overset{\|}{N}}\diagdown_{X}}{\overset{|}{CH_2}}}{\overset{\overset{OH}{|}}{C}}-\overset{\overset{O}{\|}}{C}-CH=CH-R^2 \quad (I)$$

| $R^1$ | $R^2$ | X |
|---|---|---|
| $-\underset{CH_3}{\overset{CH_3}{\overset{|}{C}}}-CH_3$ | (2-thienyl) | N |
| $-\underset{CH_3}{\overset{CH_3}{\overset{|}{C}}}-CH(CH_3)_2$ | " | N |
| $-\underset{CH_3}{\overset{CH_3}{\overset{|}{C}}}-C_2H_5$ | " | N |
| $-\underset{CH_3}{\overset{CH_3}{\overset{|}{C}}}-C(CH_3)_3$ | " | N |
| $-\underset{CH_3}{\overset{CH_3}{\overset{|}{C}}}-CH_3$ | (4-F-phenyl) | N |
| $-\underset{CH_3}{\overset{CH_3}{\overset{|}{C}}}-CH_3$ | (4-biphenyl) | N |
| $-\underset{CH_3}{\overset{CH_3}{\overset{|}{C}}}-CH=CH_2$ | (2-thienyl) | N |

TABLE 1-continued $$R^1-\underset{\underset{\underset{N}{\overset{\|}{N}}\diagdown_{X}}{\overset{|}{CH_2}}}{\overset{\overset{OH}{|}}{C}}-\overset{\overset{O}{\|}}{C}-CH=CH-R^2 \quad (I)$$

| $R^1$ | $R^2$ | X |
|---|---|---|
| (1-methylcyclohexyl) | (4-Cl-phenyl) | N |
| (1-methylcyclopentyl) | " | N |
| (1-ethylcyclopentyl) | " | N |
| $-\underset{CH_3}{\overset{CH_3}{\overset{|}{C}}}-phenyl$ | " | N |
| $-\underset{CH_3}{\overset{CH_3}{\overset{|}{C}}}-CH_2F$ | (4-Cl-phenyl) | N |
| $-\underset{CH_2F}{\overset{CH_2F}{\overset{|}{C}}}-CH_3$ | " | N |
| $-\underset{CH_3}{\overset{CH_3}{\overset{|}{C}}}-CH_3$ | " | CH |
| $-\underset{CH_3}{\overset{CH_3}{\overset{|}{C}}}-CH_2Cl$ | " | N |
| $-\underset{CH_3}{\overset{CH_3}{\overset{|}{C}}}-CH=CH-Cl$ | " | N |
| $-\underset{CH_2Cl}{\overset{CH_2Cl}{\overset{|}{C}}}-CH_3$ | " | N |
| $-\underset{CH_3}{\overset{CH_3}{\overset{|}{C}}}-(4-Cl-phenyl)$ | (4-Cl-phenyl) | N |

TABLE 1-continued $$\underset{\underset{N \diagdown X \diagup}{\underset{|}{CH_2}}}{\overset{OH}{\underset{|}{R^1-C}}-\overset{O}{\overset{\|}{C}}-CH=CH-R^2} \quad (I)$$

| R¹ | R² | X |
|---|---|---|
| 2-Cl, 4-Cl-C₆H₃-C(CH₃)₂- | " | N |
| 4-F-C₆H₄-C(CH₃)₂- | " | N |
| -C(CH₂Cl)₂CH₃ | " | CH |
| 2-F, 4-F-C₆H₃-C(CH₃)₂- | " | N |
| C₆H₅- | " | N |
| 4-F-C₆H₄- | 4-Cl-C₆H₄- | N |
| 2,4-F₂-C₆H₃- | " | N |
| 4-Cl-C₆H₄- | " | CH |
| 2,4-Cl₂-C₆H₃- | " | N |
| 2,4-Cl₂-C₆H₃- | " | CH |
| 2,4-Cl₂-C₆H₃- | 2,4-Cl₂-C₆H₃- | CH |
| 2-CH₃, 4-Cl-C₆H₃- | 4-Cl-C₆H₄- | N |
| 2-Cl-C₆H₄- | 4-Cl-C₆H₄- | N |
| " | 4-CF₃-C₆H₄- | N |
| " | 4-OCF₃-C₆H₄- | N |
| " | 4-SCF₃-C₆H₄- | N |
| " | 4-(CH=NOCH₃)-C₆H₄- | N |
| " | 4-COOCH₃-C₆H₄- | N |
| " | 4-CN-C₆H₄- | N |
| " | 4-O-C₂H₅-C₆H₄- | N |

If 4,4-dimethyl-3-hydroxy-3-[(1,2,4-triazol-1-yl)-methyl]-1-pentine is used as a starting material, sulphuric acid and mercury (II) acetate as a reaction accelerator in the first step and 4-chlorobenzaldehyde as a reaction component in the second step, the course of the process according to the invention can be illustrated by the following equation:

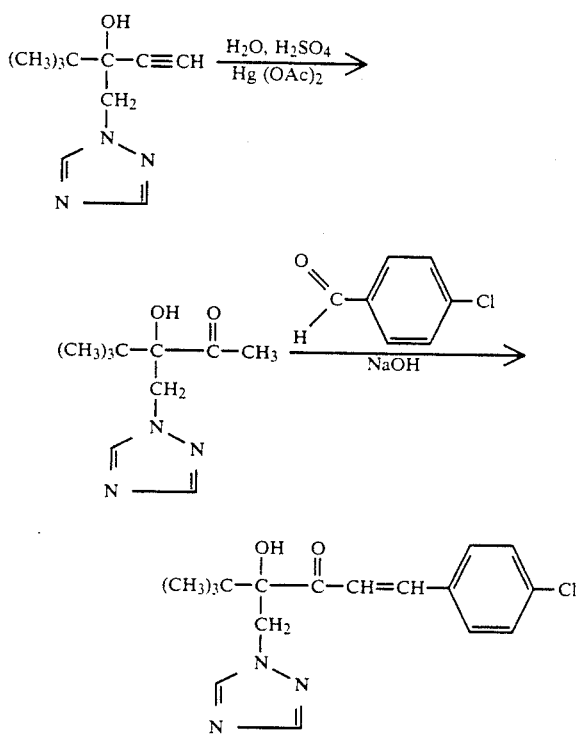

Formula(II) provides a general definition of the hydroxyalkines required as starting materials for carrying out the process according to the invention. In this formula, $R^1$ and $X$ preferably have those meanings which have already been mentioned as preferred for these radicals in connection with the description of the substances of the formula (I) according to the invention.

The hydroxyalkines of the formula(II) are already known (c.f. EP-OS (European Published Specification) 0,304,552).

Water is used as the reaction component in the first step of the process according to the invention.

Suitable reaction accelerators for carrying out the first step of the process according to the invention are all acids and/or metal catalysts customary for hydrations of this type. Acids which may preferably be used are sulphuric acid, phosphoric acid, hydrochloric acid, hydrobromic acid, nitric acid, trichloroacetic acid, trifluoroacetic acid and also acidic ion exchange resins. Metal catalysts which may preferably be used are heavy metal salts and oxides such as mercury(II) sulphate, mercury(II) acetate, mercury(II) chloride, mercury(II) oxide, copper(II) sulphate and copper(I) chloride.

Suitable diluents for carrying out the first step of the process according to the invention are water and all customary inert organic solvents.

Those which may preferably be used are water, furthermore alcohols, such as ethanol and butanol, additionally ethers, such as dioxane, furthermore acids such as acetic acid and moreover ketones, such as acetone. Mixtures of these solvents with water may also be employed.

The reaction temperatures can be varied within a relatively wide range when carrying out the first step of the process according to the invention. In general, the reaction is carried out at temperatures between 0° C. and 150° C., preferably between 20° C. and 120° C.

The first step of the process according to the invention is in general carried out under normal pressure. However, it is also possible to work at elevated or reduced pressure.

When carrying out the first step of the process according to the invention, in general 4 to 10 moles of water and a catalytic amount of acid and/or metal catalyst are employed per mole of hydroxyalkine of the formula (II). Working up is carried out by customary methods. In general, a procedure is used in which the reaction mixture is diluted with an organic solvent which is poorly soluble in water, washed with an aqueous basic solution, then dried and concentrated and the product obtained is optionally subjected to further purification methods. The hydroxyketones of the formula (III) were hitherto unknown.

Formula (IV) provides a general definition of the aldehydes required as reaction components for carrying out the second step of the process according to the invention. In this formula, $R^2$ preferably has those meanings which have already been mentioned as preferred for this radical in connection with the description of the substances of the formula (I) according to the invention.

The aldehydes of the formula (IV) are generally known compounds of organic chemistry.

Suitable catalysts for carrying out the second step of the process according to the invention are all reaction accelerators customary for condensations of this type. Those which can be preferably used are basic substances, for example alkaline metal hydroxides such as sodium hydroxide and potassium hydroxide.

Possible diluents for carrying out the second step of the process according to the invention are all inert organic solvents customary for reactions of this type. Those which can be preferably used are alcohols such as methanol, ethanol, isopropanol, n-butanol and tert.-butanol and water, if appropriate in a mixture with alcohols.

The reaction temperatures can be varied within a relatively wide range when carrying out the second step of the process according to the invention. In general, the reaction is carried out at temperatures between 0° C. and 100° C., preferably between 10° C. and 80° C.

The second step of the process according to the invention is in general carried out under normal pressure. However, it is also possible to work at elevated or reduced pressure.

When carrying out the second step of the process according to the invention, in general 0.5 to 1.0 mole of aldehyde of the formula (IV) and a catalytic amount of reaction accelerator are employed per mole of hydroxyketone of the formula (III). Working up is carried out by customary methods. In general, a procedure is used in which an organic solvent which is poorly soluble in water is added to the reaction mixture, and the mixture is washed several times with water, then dried and concentrated. To remove impurities which may still be present, the product obtained can be subjected to further purification measures.

In a particular variant, the process according to the invention can also be carried out in such a way that the hydroxyketone of the formula (III) occurring as an intermediate is not isolated, but directly reacted further.

The hydroxy-keto-azoles of the formula (I) which can be prepared by the process according to the invention can be converted into acid addition salts or metal salt complexes.

In order to prepare acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and are isolated in a known manner, for example by filtering off, and, if appropriate, purified by washing with an inert organic solvent.

To prepare metal salt complexes of the compounds of the formula (I), suitable salts of metals are preferably those which have already been mentioned as preferred metal salts in connection with the description of the metal salt complexes according to the invention.

The metal salt complexes of compounds of the general formula (I) can be obtained in a simple manner by customary methods, for example by dissolving the metal salt in alcohol, for example ethanol, and adding to compounds of the general formula (I). Metal salt complexes can be purified in a known manner, for example by filtering off, isolating and, if appropriate, by recrystallizing.

The active compounds according to the invention have a strong microbicidal action and can be employed as fungicides in plant protection and in the protection of materials.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubense;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*
(conidia form: Drechslera, syn: Helminthosporium);
Cochliobolus species, such as *Cochliobolus sativus;*
(conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;* Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The substances according to the invention are suitable, in particular, for combating cereal and rice diseases. Thus, powdery mildew and rust diseases, *Puccinia recondita, Leptosphaeria nodorum, Pyrenophora teres, Cochliobolus sativus* and *Erysiphe graminis* on cereals and also Pyricularia and Pellicularia on rice can be particularly well combated. The substances can additionally be very well employed against Venturia on apples and against Botrytis on beans; they furthermore possess a very good in vitro action.

In the protection of materials, the active compounds according to the invention can be employed for the protection of industrial materials. Industrial materials in this connection are taken to mean non-living materials which have been prepared for use in industry. For example, industrial materials which it is intended to protect from microbial change or destruction by means of the active compounds according to the invention may be adhesives, glues, paper, cardboard, textiles, leather, wood, paints, plastic articles, cooling lubricants and other materials which can be attacked or decomposed by microorganisms. In the context of the materials to be protected, parts of production plants, for example cooling water circulations, which may be impaired by replication of microorganisms, may also be mentioned. In the context of the present invention, industrial materials which may be preferably mentioned are adhesives, glues, papers and cardboard, leather, wood, paints, cooling lubricants and cooling circulations, particularly preferably wood.

Microorganisms which may be mentioned which can cause degradation of or a change in the industrial materials are, for example, bacteria, fungi, yeasts, algae and slime organisms. Preferably, the active compounds according to the invention act against fungi, in particular Hyphomycetes, wood-discoloring and wood-destroying fungi (Basidiomycetes), and also against slime organisms and algae.

Examples which may be mentioned are microorganisms of the following orders:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporous, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such, or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When using the substances according to the invention as fungicides, the amount applied can be varied within a relatively wide range depending on the application. Thus in the treatment of parts of plants, the active compound concentrations in the use forms can be varied within a substantial range. They are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and the use of the active compounds according to the invention is illustrated by the following examples.

PREPARATION EXAMPLES

Example 1

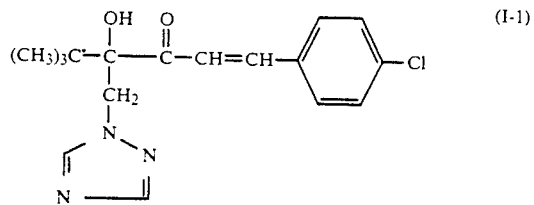

First Step

A mixture of 19.3 g (0.1 mol) of 4,4-dimethyl-3-hydroxy-3-[(1,2,4-triazol-1-yl)-methyl]-1-pentine, 200 ml of ethanol, 10 ml of water, 20 ml of concentrated sulphuric acid and 5 g of mercury(II) acetate is heated under reflux for 5 hours. The reaction mixture is then allowed to cool to room temperature and is diluted with methylene chloride, and the mixture is washed several times with dilute aqueous sodium hydroxide solution. The organic phase is dried over sodium sulphate and concentrated under reduced pressure. 20.3 g (80% of theory) of 4,4-dimethyl-3-hydroxy-[(1,2,4-triazol-1-yl)-methyl]-pentan-2-one of the formula

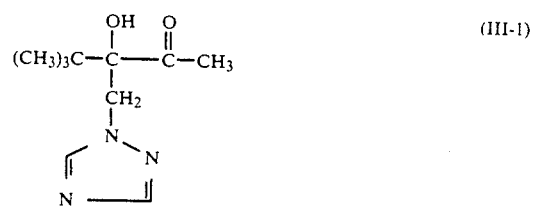

are obtained in this way in the form of a solid substance of melting point 80° to 83° C. After recrystallization from toluene, the compound has a melting point of 96° to 97° C.

$^1$H-NMR-spectrum (CDCl$_3$): 1.1 (s, 9H); 2.2 (s, 3H); 4.2 (d, J=13 Hz, 1H); 4.6 (OH), 4.85 (d, J=13 Hz, 1H); 7.9 (s, 1H); 8.05 (s, 1H)

The compounds listed by formula in the following table are also prepared according to the above described method.

TABLE 2

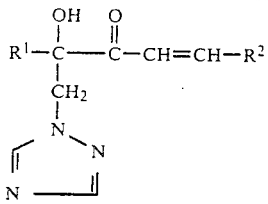

| Example No. | Compound No. | R$^1$ | R$^2$ | X | Melting point (°C.) |
|---|---|---|---|---|---|
| 2 | I-2 | —C(CH$_3$)$_3$ | (5-methyl-2-bromo-thiophene) | N | 118 |
| 3 | I-3 | —C(CH$_3$)$_3$ | (5-methyl-3-bromo-thiophene) | N | oil |
| 4 | I-4 | —C(CH$_3$)$_3$ | (5-methyl-furan) | N | 65–68 |
| 5 | I-5 | —C(CH$_3$)$_3$ | (2,4-dichlorophenyl) | N | 129–131 |
| 6 | I-6 | —C(CH$_3$)$_3$ | (2,4,5-trichlorophenyl) | N | oil (two isomers) |
| 7 | I-7 | (4-chlorophenyl) | (4-chlorophenyl) | N | 52–55 |

Second Step 12.7 g (60 mmol) of 4,4-dimethyl-3-hydroxy-[(1,2,4-triazol-1-yl)-methyl]-pentan-2-one and 7.1 g (50 mmol) of 4-chlorobenzaldehyde are dissolved in 100 ml of ethanol and stirred at 20° C. for 3 hours after addition of a solution of 4 g (0.1 mol) of sodium hydroxide in 10 ml of water. The reaction mixture is then diluted with methylene chloride and extracted by shaking several times with water. The organic phase is dried over sodium sulphate and concentrated by stripping off the solvent under reduced pressure. 15.2 g (91% of theory) of 1-(4-chloro-phenyl)-5,5-dimethyl-4-hydroxy-4-[(1,2,4-triazol-1-yl)methyl]-hex-1-ene-3-one are obtained in this way in the form of a solid substance which, after recrystallization from methylcyclohexane, has a melting point of 83° to 85° C.

$^1$H-NMR spectrum (CDCl$_3$): δ=1.1 (s, 9H); 4.35 (d, J=14 Hz, 1H); 5.0 (d, J=14 Hz, 1H), 5.0 (OH), 7.3–7.5 (m, 6H); 7.85 (s, 1H); 8.1 (s, 1H)

USE EXAMPLES

The compounds of the formulae indicated below were used as comparison substances in the following use examples:

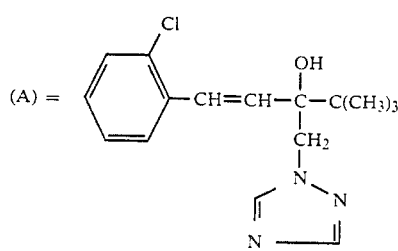

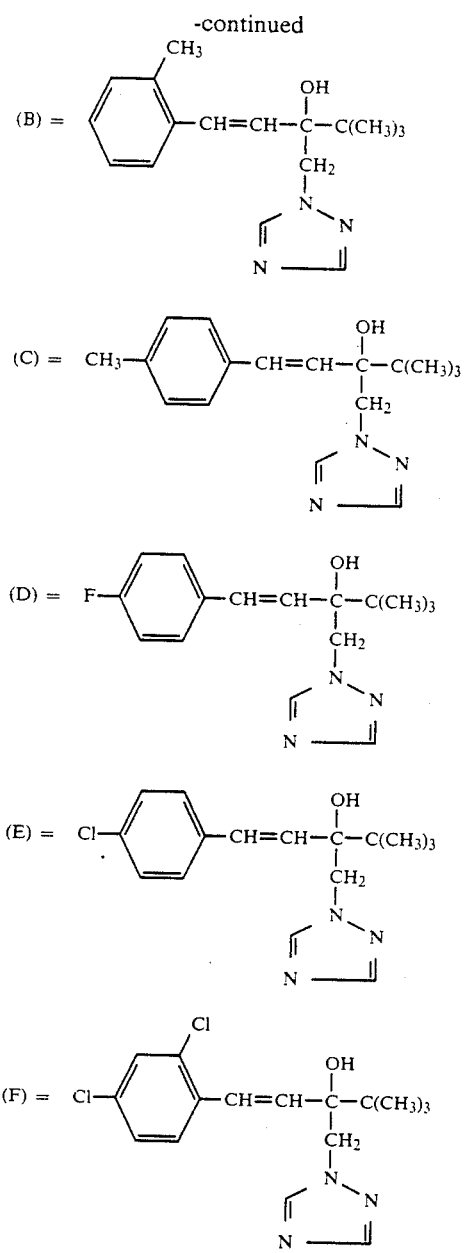

The comparison substances are known from EP-OS (European Published Specification) 0,040,345.

Example A.

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, the compounds (I-2), (I-3), (I-4), (I-5) and I-7) according to the invention show a substantial better activity than the comparison substance (A).

*Leptosphaeria Nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, the compounds (I-1) and (I-3) according to the invention show a substantially better action than the comparison substances (B), (C) and (D).

Example C

*Cochliobolus sativus* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Cochliobolus sativus*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compounds (I-1) and (I-3) according to the invention show a substantially better action than the comparison substances (B), (E) and (F).

Example D

Venturia test (apples)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound (I-1) according to the invention shows a substantially better activity than the comparison substance (E).

Example E

Botrytis test (bean)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened, humid chamber at 20° C.

3 days after the inoculation, the size of the infected spots on the leaves is evaluated.

In this test, the compounds (I-1), (I-3) and (I-5) according to the invention show a substantially better activity than the comparison substance (F).

It will be appreciated that the instant specification and claims are set forth by way of illustration and not limitation, and that various modifications and changes may be made without departing from the spirit and scope of the present invention.

What is claimed is:

1. A hydroxy-keto-azole of the formula

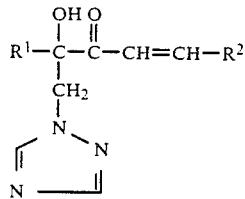

in which

R¹ represents isopropyl, tert.-butyl, tert.-pentyl, 1-ethyl-1-methyl-propyl, 1,1-dimethyl-pentyl, 1,1,2-trimethylpropyl or 1,1-dimethyl-prop-2-enyl, where each of these radicals can be mono- or disubstituted by identical or different substituents selected from the group consisting of fluorine, chlorine, phenyl and chlorophenyl, or R¹ represents 1-methyl-cyclohexyl, cyclohexyl, 1-methyl-cyclopropyl, cyclopropyl, 1-methyl-cyclopentyl, cyclopentyl or 1-ethyl-cyclopentyl, or R¹ represents phenyl which can be monosubstituted or trisubstituted by identical or different substituents from the group consisting of fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and cyano, R² represents phenyl which can be monosubstituted to trisubstituted by identical or different substituents from the group consisting of fluorine, chlorine, bromine, methyl, ethyl, tert.-butyl, methoxy, ethoxy, methylthio, trifluoromethyl, trifluoromethylthio, chlorodifluoroethoxy, chlorodifluoromethylthio, methoxycarbonyl, ethoxycarbonyl, methoximinomethyl, 1-methoximinoethyl, nitro and cyano, or R² represents pyrazolyl, imidazolyl, 1,2,4-triazolyl, pyrrolyl, furanyl, thienyl, indolyl, benzothienyl, benzofuranyl, or benzimidazolyl, where each of these radicals can be monosubstituted or trisubstituted by identical or different substituents from the group consisting of fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl, or an addition product thereof with an acid or metal salt.

2. A hydroxy-keto-azole or addition product thereof according to claim 1, in which R¹ represents tert.-butyl, tert.-pentyl, 1-ethyl-1-methylpropyl, 1,1,2-trimethylpropyl, 1,1-dimethylpentyl or 1,1-dimethyl-prop2-enyl, where each of these radicals can be monosubstituted or disubstituted by fluorine and/or chlorine, or by phenyl and/or chlorophenyl, furthermore 1-methyl-cyclohexyl, 1-methyl-cyclopentyl or 1-ethyl-cyclopentyl, or phenyl which can be monosubstituted to trisubstituted by identical or different substituents from the group consisting of fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, nitro, cyano and methoximinomethyl, and R² represents phenyl which can be monosubstituted to trisubstituted by identical or different substituents from the group consisting of fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, nitro, cyano and methoximinomethyl, or R² represents furanyl, thienyl, benzothienyl, or benzofuranyl, where each of these radicals can be monosubstituted to trisubstituted by identical or different substituents from the group consisting of fluorine, chlorine, bromine, methyl, ethyl, methoxy, ethoxy, methylthio, trifluoromethyl, trifluoromethoxy, trifluoromethylthio, hydroxymethyl, 3-hydroxy-3-methylbut-1-yn-1-yl, methoxycarbonyl, ethoxycarbonyl, formyl, dimethoxymethyl, methoximinoethyl, methoximino-ethyl, nitro and cyano.

3. A compound according to claim 1, wherein such compound is 1-(4-chlorophenyl)-5,5-dimethyl-4-hydroxy-4-[(1,2,4-triazol-1-yl)-methyl]-hex-1-ene-3-one of the formula

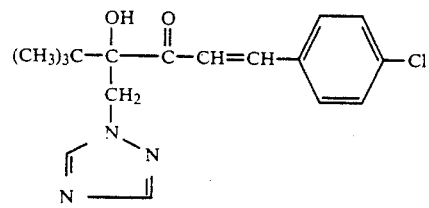

(I-1)

or an addition product thereof with an acid or metal salt.

4. A compound according to claim 1, wherein such compound is 1-(5-bromo-thien-2-yl)-5,5-dimethyl-4-hydroxy-4[(1,2,4-triazol-1-yl)-methyl]-hex-1-ene-3-one of the formula

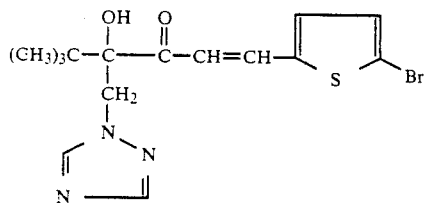

or an addition product thereof with an acid or metal salt.

5. A compound according to claim 1, wherein such compound is 1-(4-bromo-thien-2-yl)-5,5-dimethyl-4-hydroxy-4-[(1,2,4-triazol-1-yl)-methyl]-hex-1-ene-3-one of the formula

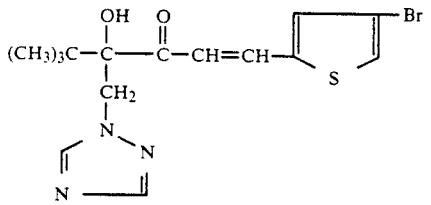

or an addition product thereof with an acid or metal salt.

6. A compound according to claim 1, wherein such compound is 1-(2,4-dichloro-phenyl)-5,5-dimethyl-4-hydroxy-4-[(1,2,4-triazol-1-yl)-methyl]-hex-1-ene-3-one of the formula

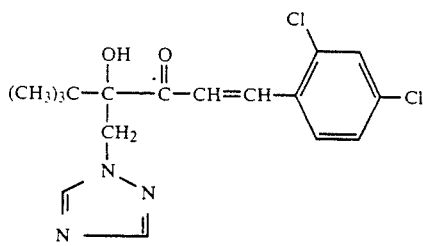

or an addition product thereof with an acid or metal salt.

7. A compound according to claim 1, wherein such compound is 1,4- bis-(4-chloro-phenyl)-4-hydroxy-5(1,2,4-triazol-1-yl)-pent-1-ene-3-one of the formula

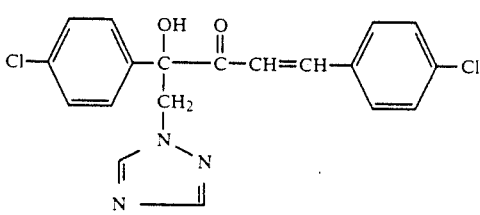

or an addition product thereof with an acid or metal salt.

8. A microbicidal composition comprising a microbicidally effective amount of a compound or addition product thereof according to claim 1 and an inert diluent.

9. A method of combating microbes which comprises applying to such microbes or to a locus from which it is desired to exclude such microbes a microbicidally effective amount of a compound or addition product thereof according to claim 1.

10. The method according to claim 9, wherein such compound is
1-(4-chlorophenyl)-5,5-dimethyl-4-hydroxy-4[(1,2,4-triazol-1-yl)-methyl]-hex-1-ene-3-one,
1-(5-bromo-thien-2-yl)-5,5-dimethyl-4-hydroxy-4[(1,2,4-triazol-1-yl)-methyl]-hex-1-ene-3-one,
1-(4-bromo-thien-2-yl)-5,5-dimethyl-4-hydroxy4-[(1,2,4-triazol-1-yl)-methyl]-hex-1-ene-3-one,
1-(2,4-dichloro-phenyl)-5,5-dimethyl-4-hydroxy-4-[(1,2,4-triazol-1-yl)-methyl]-hex-1-ene-3-one, or
1,4- bis-(4-chloro-phenyl)-4-hydroxy-5-(1,2,4-triazol-1-yl)-pent-1-ene-3-one,
or an addition product thereof with an acid or metal salt.

* * * * *